(12) United States Patent
Jaeger et al.

(10) Patent No.: US 8,967,819 B2
(45) Date of Patent: Mar. 3, 2015

(54) LIGHT CURING DEVICE

(75) Inventors: Sonja Jaeger, Mauren (LI); Wolfram Murr, Chur (CH)

(73) Assignee: Ivoclar Vivadent AG, Schaan (LI)

( * ) Notice: Subject to any disclaimer, the term of this patent is extended or adjusted under 35 U.S.C. 154(b) by 373 days.

(21) Appl. No.: 13/476,298

(22) Filed: May 21, 2012

(65) Prior Publication Data

US 2012/0321736 A1 Dec. 20, 2012

(30) Foreign Application Priority Data

May 24, 2011 (EP) ..................................... 11167289

(51) Int. Cl.
- *G01D 11/28* (2006.01)
- *F21V 33/00* (2006.01)
- *A61C 13/15* (2006.01)

(52) U.S. Cl.
CPC .................................... *A61C 19/004* (2013.01)
USPC ...................... 362/23.05; 362/23.08; 362/109; 200/314

(58) Field of Classification Search
CPC ................. A61C 19/004; A61C 1/088; A61N 2005/0652; A61N 2005/0644
USPC ................. 362/23.04, 23.05, 249.05, 249.12, 362/249.13, 295, 23.07, 23.08, 109, 119; 200/314, 315; 433/29
See application file for complete search history.

(56) References Cited

U.S. PATENT DOCUMENTS

| | | | |
|---|---|---|---|
| 5,912,470 A | 6/1999 | Eibofner et al. | |
| 6,278,069 B1 | 8/2001 | Lee et al. | |
| 6,331,111 B1 * | 12/2001 | Cao | 433/29 |
| 6,572,637 B1 * | 6/2003 | Yamazaki et al. | 607/89 |
| 6,709,128 B2 * | 3/2004 | Gordon et al. | 362/119 |
| 7,170,018 B2 * | 1/2007 | Ilkhanov | 200/18 |
| 7,267,457 B2 * | 9/2007 | Ostler et al. | 362/294 |
| 8,113,831 B2 | 2/2012 | Plank et al. | |
| 8,289,716 B2 * | 10/2012 | Patel et al. | 361/728 |
| 8,459,812 B2 * | 6/2013 | Wu et al. | 362/23.01 |
| 2006/0188835 A1 * | 8/2006 | Nagel et al. | 433/29 |
| 2010/0101924 A1 * | 4/2010 | Wu et al. | 200/339 |

FOREIGN PATENT DOCUMENTS

DE 102006035658 2/2008

* cited by examiner

*Primary Examiner* — Thomas M Sember
(74) *Attorney, Agent, or Firm* — Ann M. Knab; Thad McMurray

(57) ABSTRACT

A light curing device (10) for dental purposes which is provided with a housing (12), at least one control element for controlling the operation of the light curing device and an actuating member (26) which is mounted moveably relative to the housing for the actuation of the control element. The light curing device is provided with at least two control elements (44, 46) spaced apart from each other which are electrically connected in parallel. Furthermore, at least one of the control elements (44, 46) can be actuated by actuation of the actuating member (26).

25 Claims, 5 Drawing Sheets

LIGHT CURING DEVICE

CROSS-REFERENCE TO RELATED APPLICATIONS

This application claims the benefit of European Patent Application No. 11167289.5 filed May 24, 2011, which is hereby incorporated by reference in its entirety.

TECHNICAL FIELD

The present invention relates generally to a light curing device for dental purposes, and in particular, to a hand-held light curing device.

BACKGROUND

In the dental industry, light curing devices serve to polymerize polymerizable dental restorations. For this purpose, the device is provided with a light source whose light emission is attuned to the dental restoration material to be cured. As dental restorations have to be mounted at most various places in the upper jaw and lower jaw in the mouth of a patient easy handling and application of the light curing device in various positions relative to the mouth of the patient are indispensable.

In order to guarantee an ergonomic handling such light curing devices have substantially the shape of a pistol or of a rod. Besides the light source, the housing of the light curing device must also receive energy sources such as accumulators, and the control electronics for the realization of the polymerization cycle.

The basic design of such a light curing device is disclosed in DE 10 2006 035 658 A1 and corresponding U.S. Pat. No. 8,113,831 (B2), which is hereby incorporated by reference. The light curing device described is provided with an actuation switch at its bottom side with a pushbutton function, and at its top side which is facing the operator, a display device.

Such display devices are important in order to give the operator quickly discoverable and brief information on the exposure state but also, for example, to inform the operator if the available residual capacity of the energy storage unit is sufficient for the desired polymerization cycle.

While the release button of the disclosure mentioned can practically only be pressed with the index finger of the operator, or possibly with his or her middle finger, today especially young dentists wish to operate the release button with their thumb. This means that it is appropriate that the button concerned is attached closer to the top of the dental light curing device, as is the case with rod-shaped light curing devices anyway.

While a button, which is mounted to the bottom side of the light curing device in the manner of the trigger of a pistol, is actuated almost automatically due to the natural way of holding the device, with a button on the top this is only the case when the operator aims at the button with his or her finger in a targeted manner. In this connection, it must be taken into consideration that the dentist directs his attention primarily not to the device but to the mouth of the patient and the dental restoration which is located there and needs to position the light exiting end of the light curing device precisely at the right spot and to hold the device continuously, at least during the light curing.

In order to still make possible a reliable release of the button, it has been suggested to enlarge the size of the release button.

Surprisingly enough, the operability is even worse with a larger release button so that the producers of light curing devices almost exclusively use a release button whose size is not larger than the size of a human finger tip, for example, a diameter of less than 8 mm.

SUMMARY

Therefore, it is the object of the invention to create a light curing device which can be operated securely and which still provides the possibility of showing additional information.

It is especially favorable according an embodiment of the present invention that a relatively large actuating member can be used for the operation of the light curing device which has an effect on two electric control elements which are connected in parallel. The control elements are spaced apart from each other. At least one part of the actuating member extends, viewed from above in the projection, between the control elements which creates a distance between the control elements.

According to an embodiment of the present invention it is especially favorable that a relatively large actuating surface is available with the actuating member. This surface can extend in parallel to the surface of the housing, preferably substantially parallel or slanted to the longitudinal axis of the light curing device. It is preferable that the curing light contains no more than one actuating member and wherein at least one of the control elements or both control elements together can be actuated by actuation of the single actuating member.

Even if the operator actuates the button "blindly", he or she does not miss the actuating surface of the actuating member.

The actuation will not lead to tilting according to an embodiment of the present invention. If, contrary to the invention, only one control element is used for the release of the electric switching operation, which is for example, disposed centrally below the actuating member, this would lead to pressure on the edge of the actuating member and a tilting of the related switching element like a plunger of the control element. This is prevented according to an embodiment of the present invention by the use of two control elements; independent of which place the actuating member is pressed down, one of the control elements, or possibly both, releases and provides the control function which is necessary for the operation of the light curing device.

In an especially favorable development of an embodiment of the invention control elements with a relatively small actuating force can be used. The actuating force must be at least as large as the weight of the actuating member and the related switching elements, and must additionally comprise a safety margin. If, for example, the total weight of these elements amounts to 20 g, an actuating force of 1 Newton per control element is easily enough as the total reset force will then amount to 2 Newton, i.e. about a tenfold of the mentioned weight.

In an advantageous development of an embodiment of the invention the large actuating member is provided with guide elements which allow for the movement of the actuating member in actuating direction but which prevent a transverse movement. Such guide elements can e.g. be formed as pins which protrude from the actuating member and which project into through openings at an element which is fixed to the housing. The element which is fixed to the housing can, for example, be a printed circuit which also supports the control elements.

The limitation of the actuating path of the actuating member can be formed—if necessary, either by the guide elements likewise or by the housing or another element which is fixed to the housing which provides the desired guidance of the actuating member.

The guide elements do not prevent the actuating member from experiencing a slight tilting movement like it occurs due to the one-sided pressing down of the actuating member. The tilting angle which is insofar allowed and provided by the larger size of the through openings compared to the pins can, for example, amount to 10 degrees while the tilting angle which occurs due to the one-sided pressing down of the actuating member and which is limited by the control element is a bit smaller, for example eight degrees.

In an advantageous development the actuating member is formed as a part of the display device at the same time. For this purpose, it is at least partially transparent or translucent. Preferably, this applies at least partially for the area between the control elements, in turn as seen in the projected view from above onto the actuating member.

In order to provide for the desired display, the actuating member is preferably provided with light through openings and the printed circuit supports light emitting elements, in particular LED chips, which are in alignment with the through openings. For example, three or four LED chips and a corresponding number of light through openings can be provided which in turn extend between the control elements and which are clearly spaced apart from each other.

In order to channel the light output of the light emitting elements and to provide for an optical decoupling, the actuating member is provided with non-transparent or opaque material in the area of the light through openings. In this way, the light emitted by each LED chip enters the related light through opening of the actuating member but does not enter adjacent light through openings.

At the positions which correspond to the light through openings, the cover which is preferred by the invention is provided with markings or symbols which symbolize or signal the operating state of the light curing device or, for example, the selected exposure times. In order to control the light curing device, the operator can, for example, press down on the actuating member multiple times and in this way select the exposure time. For this, via the control device of the light curing device, the related light emitting element is turned on so that the related exposure time is illuminated from below and visible for the operator, while the other exposure times are not illuminated and therefore invisible or at least almost invisible.

In this connection it is preferred that the desired exposure time is selected by a multiple actuation of the actuating member wherein the exposure times are practically run through in a cyclical manner with the help of the actuation. It is also possible to turn on the light curing device with the help of a special actuation such as a double click, i.e. the twofold pressing down of the actuating member within a short period of time, or to trigger any other control function which corresponds to the corresponding operating state which is provided for by the control device of the light curing device.

Preferably, the actuating member is provided with a cover made of transparent or translucent material, apart from the non-transparent material. This cover extends over the non-transparent material and forms the actuating surface of the actuating member at the same time. Its shape is adapted to the outer contour of the light curing device at this point and it is in alignment with it. Preferably, however, there is a small projection compared to an exactly aligned orientation which amounts, for example, to 0.5 or 1 mm, and the cover projects by this dimension.

For actuating the actuating member the operator can immediately feel, even when actuating blindly, that he or she is pressing down on the actuating member at the correct place. The actuation stroke also amounts preferably to 1 mm so that, when pressed down, the actuating surface is in alignment with the surface of the housing or slightly below this level.

It is also especially favourable that the housing of the light curing device be provided with one break due to the whole unit comprised of the actuating member and display device according to an embodiment of the invention, and in this way it is easier to sterilize. If necessary, between the actuating member and the through opening in the housing of the light curing device which receives the actuating member a seal can be provided, which can, for example, consist of a sealing bellows which consists of elastomer and which seals in a circumferential manner without being a hindrance to the stroking movement of the actuating member. In this design the light curing device according to the invention is sealed off and can, for example, also be sterilized in a bath of sterilizer liquid.

It is especially favourable when the actuating member extends between the control elements like a rod or a bridge and is supported by supports on the switching elements, in particular the plungers, of the control elements. The plungers form the bridge piers at the same time and a safe and secure mounting is guaranteed. Preferably, the display device of the light curing device extends between the control elements where the LED chips of the display device are fixed relative to the housing. The mounting can either take place preferably on the printed circuit or discrete LEDs can also be used. The light signals, which are sent by the LEDs, exit the light curing device via the light through openings of the actuating member wherein they also pass through a transparent cover following the light through opening.

The LEDs or LED chips are preferably spaced apart from each other in the same pattern and extend between the buttons or switches which form the control elements. Above every LED chip a through opening forms in the actuating member whereas the through openings are preferably provided with such a position of height that one LED chip each extends into a through opening but, preferably, only partially. The through openings are provided with an excess relative to the LED chips so that the related LED chip and the edge of the through opening do not touch even with a tilting movement of the actuating member.

Preferably, the actuating member is provided with a length/width ratio of between 1.5 to 1 and 10 to 1 and the control elements are mounted at the ends of the long side of the actuating member. The LED chips as well as the control elements are preferably supported by the printed circuit. They can be formed as SMD elements or can be provided with connections for solder lands which are plated through.

Preferably, every control element is provided with a compression spring whose spring force, when installed, corresponds to the actuating force of the control elements. In any case, this spring force will be sufficient to press the actuating member from the inside against the housing.

As the control elements are connected in parallel a logical OR function can be realized when the control elements are actuated. As soon as one of the control elements is actuated, the corresponding switching function is triggered.

For example, the operating state of the light curing device can then be changed. In a selection mode, before the light curing device is turned on, the desired exposure time can be changed, e.g. between 10, 15, 20 and 30 seconds, and a one-time actuation of the actuating member switches the exposure time to the next exposure time, i.e., from 10 to 15, from 15 to 20, from 20 to 30 and then again to 10, so that the desired exposure times are selected by a cyclical pass through. Preferably, by actuating the actuating member a LED chip which corresponds to the exposure time is turned on and all the others are turned off.

A malfunction can, for example, be signaled by a flashing of the corresponding light emitting element, e.g. when the state of charge of the light curing device is not sufficient for the desired exposure time.

In an advantageous development the cover is formed as a separate element which corresponds with the rest of the actuating member, in particular, in a fitting manner. In this way, a well protected design for the desired control function can be provided.

With respect to the handling it is favorable that the control element actuates a control function even upon eccentric pressure, in particular also upon actuation in the fringe area. When the actuating member is pressed down at its edge, in particular adjacent to one of the control elements, this control element is actuated while the other control element is not actuated. In this way the control function is started, independent of which control element is pressed down.

In an advantageous development, the light curing device is provided with at least two control elements spaced apart from each other which are electrically connected in parallel and with at least one of the control elements able to be actuated by actuation of the actuating member.

In an advantageous development, the control elements are provided with spring-loaded switching elements which can be actuated via the actuating member, in particular, with a rocker or a plunger each.

In an advantageous development, at least one part of the actuating member extends between the control elements and, in particular, at least one part of the actuating member protrudes beyond the outer contour of the control elements.

In an advantageous development, the actuating member extends over the control elements in a beam- or bridge-like manner and is supported by them.

In an advantageous development, the actuating member is mounted moveably in the actuating direction of the control elements relative to a printed circuit which is disposed in the housing whereas the path of movement of the actuating member is limited by stops which are fixed to the housing and/or by the printed circuit and/or by stops of the control elements.

In an advantageous development, at least guide elements serve to movably store the actuating member which prevent a movement of the actuating member in a direction transverse to the actuating direction of the control elements, which, however, make possible a tilting movement of the actuating member, in particular, two pins which protrude from the actuating member project into corresponding through openings in the printed circuit.

In an advantageous development, at least one light emitting element and the control elements are attached to the printed circuit and supported by it, in particular, several light emitting elements, and that the actuating member is provided with at least one light through opening, in particular several, whose middle longitudinal axis is in alignment in particular with the light emission axis of the light emitting element.

In an advantageous development the light through openings for optically decoupling the light emitting elements from one another are provided with such a position of height that one light emitting element each projects into one light through opening.

In an advantageous development, the actuating member keeps a lateral distance relative to the light emitting elements even when actuating only one control element by pressing down one side of the actuating member.

In an advantageous development, the actuating member consists at least partially of an non-transparent or opaque material and on the side of the through openings which is opposite to the light emitting elements is provided with a cover onto which in particular markings or symbols are attached and on which particularly preferably exposure times in the form of numbers are identifiable.

In an advantageous development, the cover in front of the through openings is transparent at the positions where the markings or symbols are attached, and in particular, apart from that is non-transparent or opaque.

In an advantageous development, the cover is supported in a vertical direction by the interior of the housing and it limits the vertical movability of the actuating member.

In an advantageous development, upon actuating the actuating member the light emitting elements light up successively and in particular, the lighting up of a light emitting element symbolizes a certain operating state and/or an exposure time.

In an advantageous development, upon actuation of the switch or button the operating state of at least one light emitting element is changed as an optical confirmation, in particular, one light emitting element is turned off and an adjacent light emitting element is turned on.

In an advantageous development, the control element is formed by an electric switch or an electric button and/or the light emitting elements are formed by light diodes (LED), in particular LED chips.

In an advantageous development the cover consists of an elastic material, in particular silicone.

BRIEF DESCRIPTION OF THE DRAWINGS

Embodiments of the present invention will be more fully understood and appreciated by the following Detailed Description in conjunction with the accompanying drawings, in which.

DETAILED DESCRIPTION

Figure 1:
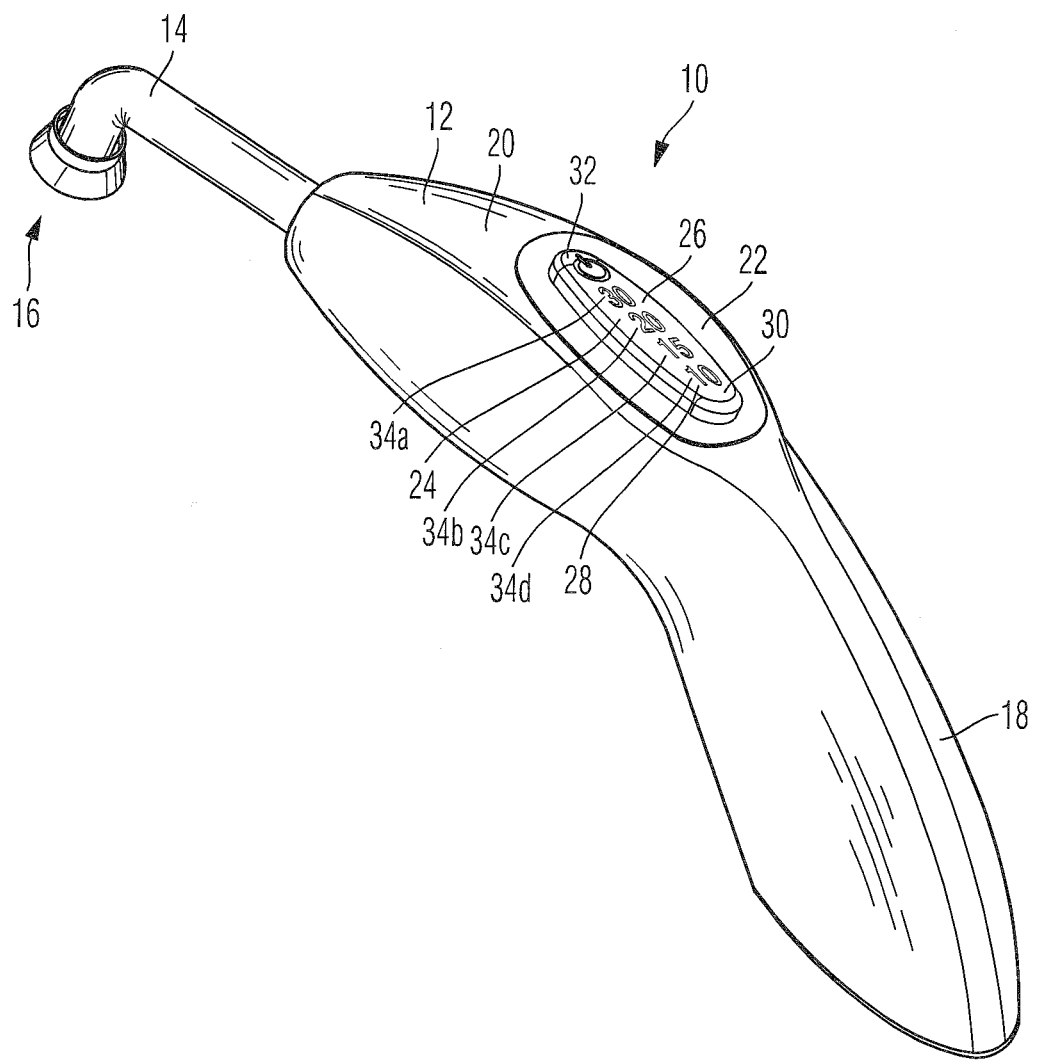
FIG. 1 is a schematic view of the light curing device in an embodiment according to the invention.

The light curing device 10 shown in FIG. 1 is provided with a housing 12 at whose front end a light guide rod 14 is attached whose end 16 is bent in a way known for the emission of light.

The housing 12 of the light curing device 10 is substantially pistol-shaped and in so far it is provided with a handle 18 and a shank 20 which are set at a tilt angle to each other, for example, at a tilt angle of 35 degrees.

On the upper side of the light curing device 10, in the area of the shank 20, but in its rear area, i.e. adjacent to the handle 18, a receipt surface 22 is formed which receives an actuating member 26 according to the invention. In the embodiment shown, the receipt surface 22 is realized by a slight protruding area relative to the rest of the housing 12. Alternatively, a transition-less realization of the receipt surface 22 is also possible, i.e. a realization in which the receipt surface 22 does not overtop or extend above the remaining housing 12.

The actuating member 26 has an oblong shape and in the embodiment shown it has the shape of the outlines of a fir cone approximately. The broader end is adjacent to the handle 18 and the narrower end is adjacent to the light guide rod 14. The actuating member 26 extends almost half the length of the shank 20 and is relatively long and large. Its lateral extension amounts to approximately one third of its longitudinal extension and takes up approximately one quarter or one third of the width of the light curing device 10.

The actuating member 26 also protrudes beyond the receipt surface 22 slightly, preferably by about 0.5 mm. It is to be understood that instead of this any other degree of protruding, e.g. of up to 2 mm, can be chosen or that in a modified embodiment the degree of protruding can also be reduced to 0.

Preferably, the actuating surface 26 of the actuating member 26 is provided with a slightly different surface structure than the rest of the housing 22. For instance, the housing 12 can consist of a very smooth plastic material, and the actuating surface 26 can have a slightly rough surface.

The actuating member 26 is additionally provided with markings 28 which are symbolically shown in FIG. 1. The markings can either be deposited in the cover 30 of the actuating member, i.e. can be realized via coloring from top or bottom, or they can have a three-dimensional shaping so that they can be felt by the finger of the operator.

In the embodiment shown, a symbol 32 is provided for turning on the light curing device, as well as four symbols 34a, 34b, 34c and 34d which are each marked with 30, 20, 15 and 10 and which symbolize the corresponding exposure times of the light curing device.

The light curing device 10 is exclusively operated via the actuation of the actuating surface 26. No matter at which spot the operator pushes down on the actuating member 26, may it be in the rear area, may it be in the front area—i.e. adjacent to the light guide rod 14, the desired operating function is released, namely a selection of the exposure time and a turning on of the light curing device for the period of time of the desired exposure time.

Figure 2:
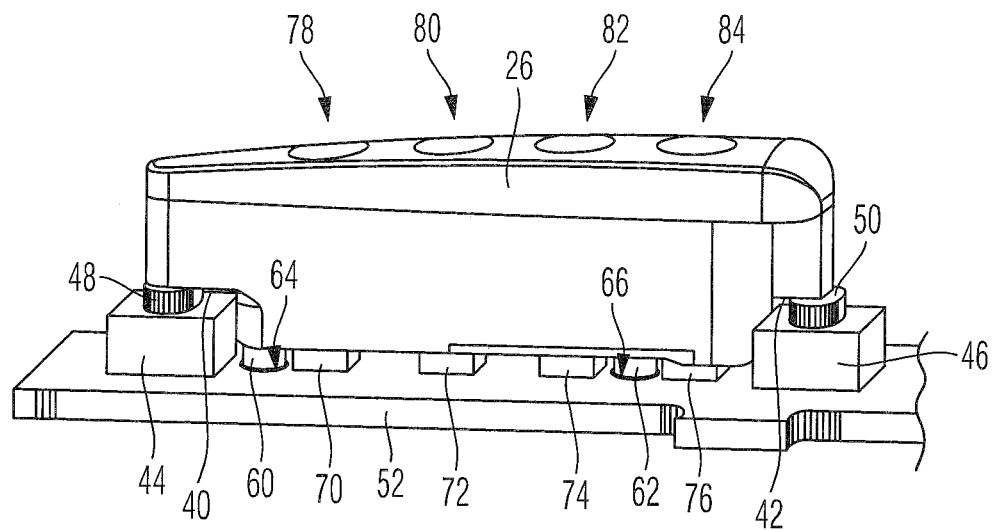
FIG. 2 is a schematic view of the actuating member and the control element as well as the printed circuit for the light curing device according to FIG. 1 in an embodiment according to the invention.

FIG. 2 discloses the practical implementation of an actuating member 26 and the associated further elements of the inventive light curing device. The actuating member 26 extends parallel to the surface of the housing 12 at the corresponding position of the housing. It is supported via supports 40 and 42 in a bridge-like manner by control elements 44 and 46, namely by their switching elements 48 and 50. Together with the associated switching element 48 or 50, each control element 44 and 46 forms an encapsulated button known per se which is soldered onto a printed circuit 52 or attached to it in any other way.

By pressing down the associated switching element 48 or 50, the desired switching function is created. The switching element is, however, pushed to the top in a confined way via one compression spring each which in turn also pushes to the top the actuating member 26 via the associated support 40 or 42.

According to the invention it is especially favorable that the actuating member 26 extends as a relatively large body, which is, however, at least partially hollow, in such a way that the area between the control elements 44 and 46 is also almost completely covered by the actuating member 26. The extensive arrangement makes possible a precise guidance of the actuating member 26. For this purpose, guide elements 60 and 62 are provided which are designed like pens and which pass through through openings 64 or 66 in the printed circuit 52. These guide elements 60 and 62 ensure a lateral guidance of the actuating member 26. A slight tilting caused by one-sided pressure on the actuating member 26 is, however, not prevented by this guidance but it does prevent a lateral movement, i.e. a movement transverse to the release direction of the control elements 44 and 46.

Slightly below the actuating member 26, i.e. between the member and the printed circuit 52, LED chips 70, 72, 74 and 76 are disposed which are attached as a surface mount device (SMD) element in a way known per se to the printed circuit 52. They protrude into the light through openings 78, 80, 82 and 84 which extend through the actuating member 26 and make possible the free light transmission.

In a way known per se, the printed circuit 52 is provided with conducting paths which provide the connections for the control elements 44 and 46 on the one hand and for the LED chips 70 to 76 on the other hand and which are connected with the control device, which is not shown, for the light curing device 10.

Figure 3:
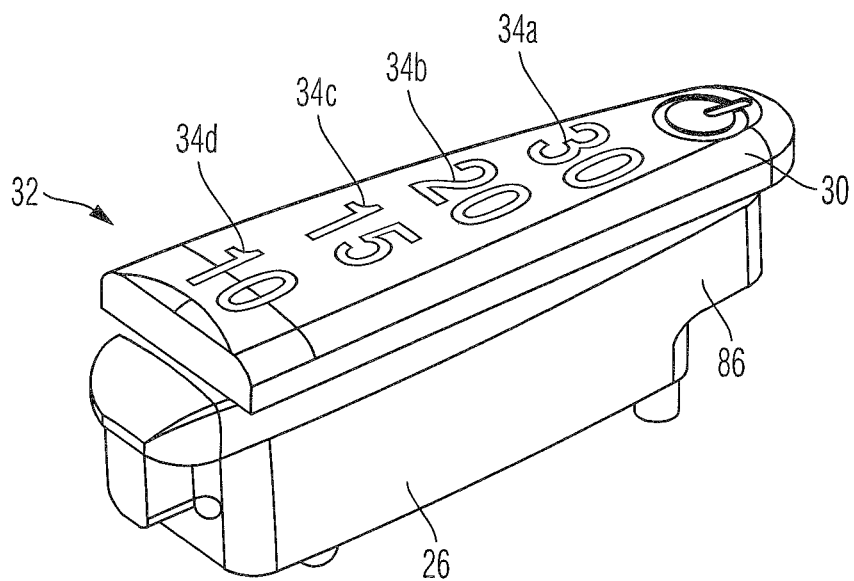
FIG. 3 is a further perspective embodiment corresponding to the embodiment of FIG. 2, whereas the cover of the actuating member can be seen.

FIG. 3 shows that the cover 30 is attached to that part of the actuating member 26 which can be seen in FIG. 2. The lower part 86 of the actuating member 26 consists of an opaque material while the cover 30 consists of a transparent or at least translucent material. The symbols 34a, 34b, 34c and 34d are each attached above the light through openings 78, 80, 82 and 84 so that the corresponding symbol 34a to 34d is lit up from below when the related LED chips 70, 72, 74 or 76 emit light, while the other symbols remain unlit.

With the help of the realization of the symbols 32 shown in this embodiment, an additional haptic signalizing for the actuation of the actuating member 26 can be realized.

Figure 4:
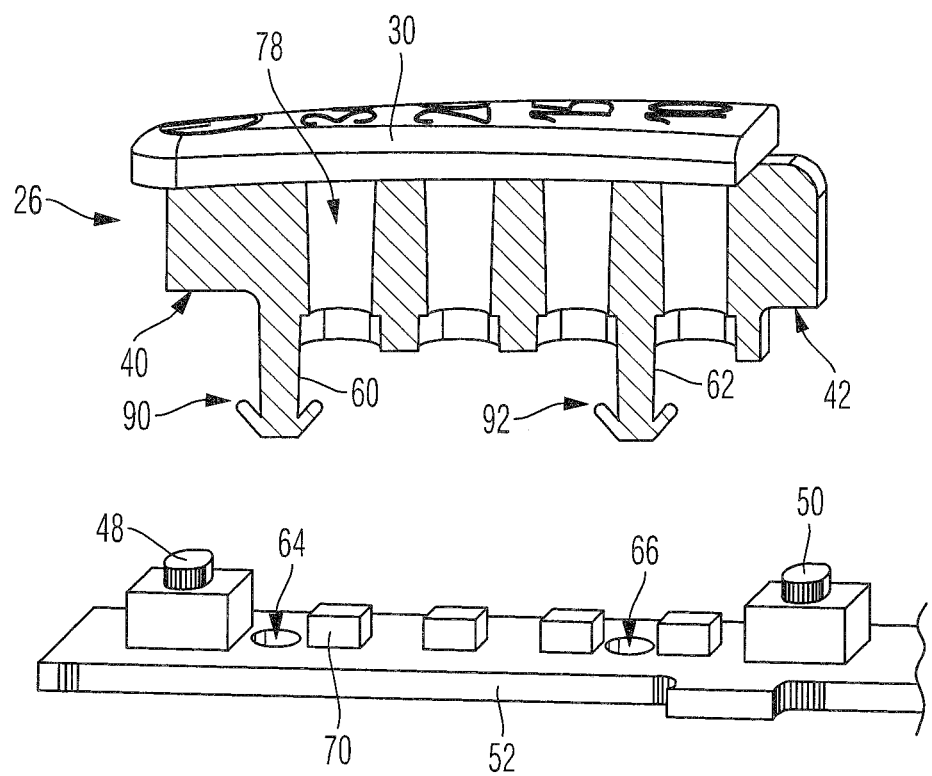
FIG. 4 is a further embodiment of an actuating member according to the invention and further elements of the light curing device according to the invention in a further embodiment.

FIG. 4 shows a modified embodiment of the actuating member 26. In this embodiment, guide elements 60 and 62 are each provided, on their rear sides, with a stop 90 or 92 which points upwards. The tongue of the stops 90 or 92, which extends in an arrow-shaped manner, can be folded up for the introduction of the guide elements 60 and 62 into the through openings 64 and 66 and spread apart after having passed through the printed circuit 52 so that a stop is formed for the actuation path of the actuating member 26 which prevents a further upward movement.

The downward movement is limited by the travel distance of the switching elements 48 and 50 which support the actuating member 26 via the supports 40 and 42. Preferably, the dimensioning of the supports 90 and 92 is provided in such a way that the supports 40 and 42 are supported by the switching elements 48 and 50 with a slight initial tensioning so that a guidance without clearance of the actuating member is realized.

As can be seen from FIG. 4, the through openings 78 are provided with a slightly larger diameter than the LED chips 70 and extend over the entire height of the actuating member 26.

Figure 5:
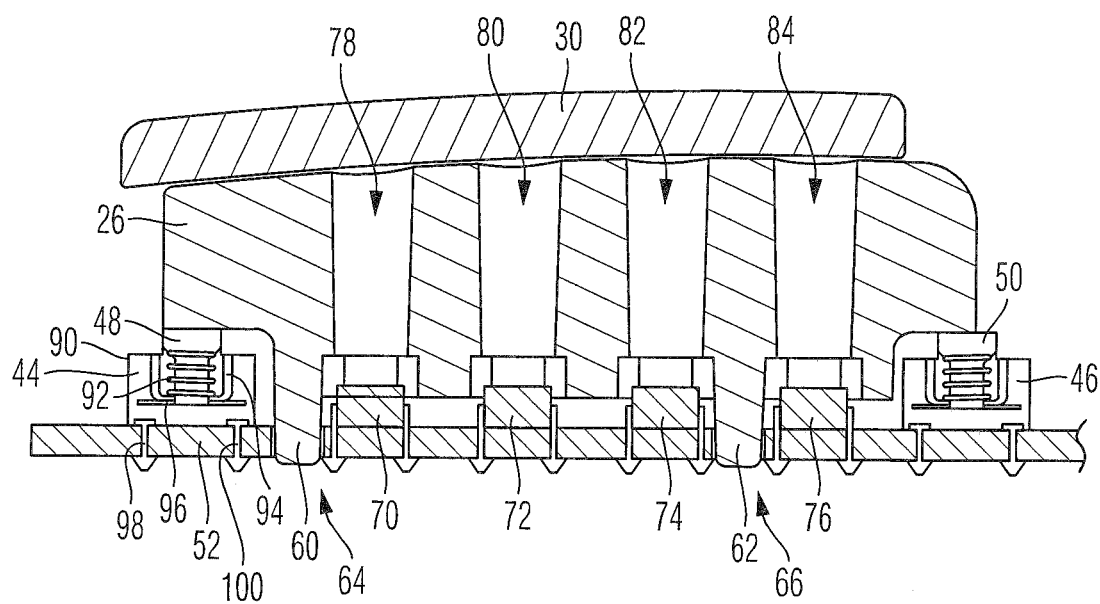
FIG. 5 is a section through the actuating member and further elements of the light curing device according to the invention corresponding to the embodiment according to FIG. 2.

An enlarged illustration of an inventive actuating member 26 and further elements of the inventive light curing device can be seen from FIG. 5. Here, as well as in the other figures, the same parts indicate the same or corresponding elements. In this embodiment, the control elements and the LED chips 70 to 76 which are shown in the embodiment are provided with connecting wires which each protrude into and pass through the corresponding opening recesses in the printed circuit 52, and, at the opposite end which is shown as the lower end in the embodiment, they are soldered up with corresponding conductor paths.

Each control element 46, which is formed as a button, is provided in a way known per se with a switching element 48 which comprises a plunger. The design is explained with the help of the control elements 44 and 46. The plunger 48 projects from the housing 90 of the control element 44 to the top. In the interior of the housing it is surrounded by a compression spring 92 which pushes the plunger 48 to the top and whose bottom is supported by a cylinder 94 which is fixed to the housing. The switching element 48 passes through the cylinder 94 which switching element is provided with a contact plate 96 which extends substantially parallel to the printed circuit, i.e. above the two contacts 98 and 100.

When pressing down on the switching element 48 the contact plate 96 now short-circuits the contacts 98 and 100 so that the control function is provided in the desired way.

Via corresponding conductor paths the contacts 98 and 100 of the control element 44 are connected in parallel to the contacts of the control element 50.

In the embodiment shown the cover 30 runs slightly inclined to the printed circuit 52. Due to the relatively largely dimensioned design of the actuating member 26, in this way, the outline can be realized without further ado whereas it is to be understood that a parallel arrangement is also possible without further ado depending on the design of the inventive light curing device 10.

Figure 6:
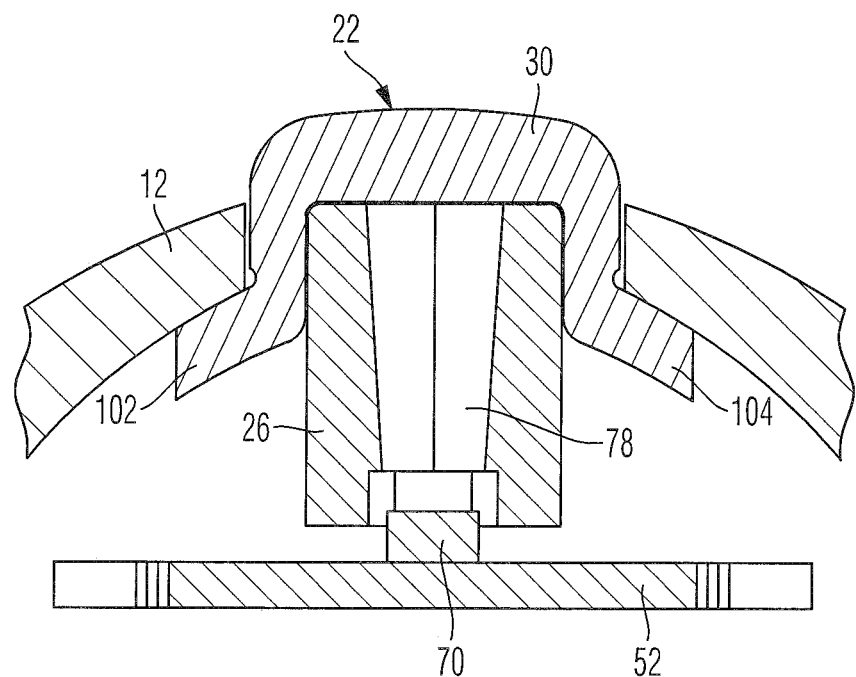
FIG. 6 is a modified embodiment of a light curing device according to the invention, showing a part of the actuating member in a cross-section.
Figure 7:
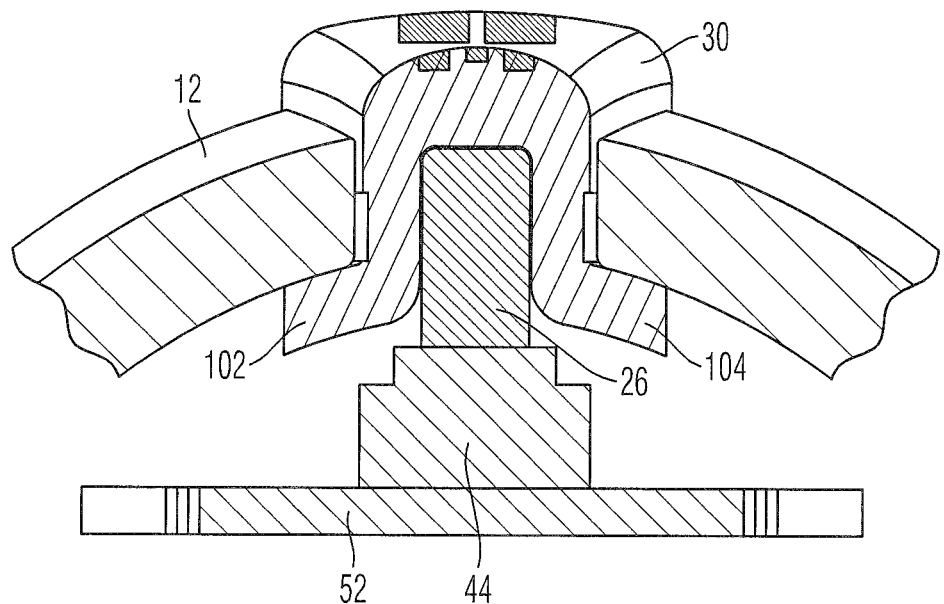
FIG. 7 is a section corresponding to the embodiment according to FIG. 6, however, at another place, whereas the control element is shown in a section.

FIGS. 6 and 7 show a modified embodiment of the invention. This embodiment differs from the further embodiments as it is provided with another type of cover. This cover 30 consists of an elastomer or another soft elasticity plastic material and extends in a sectional view in a substantially hat-shaped manner over the remaining actuating member 26. The cover 30 extends in a way known through an opening recess in the housing 12. It protrudes considerably relative to the surface of the housing, e.g. by 1 or 2 mm. Lateral flanges 102 and 104 extend in the interior of the housing along the wall of the housing, basically in its extension. In this way, an especially good sealing can be realized, especially when there is an initial tensioning at the contact surface between the flange 102 and 104 and the housing 12 which remains even when the actuating member 26 is pressed down onto the receipt surface 22.

The through opening 78 is fed with light from the light source 70 which is attached to the printed circuit 52, as is also the case in the aforementioned embodiments. The cover 30 is transparent or translucent; it can, for instance, consist of a silicone-like material. When the LED chip 70 emits light, the part of the cover 30 which extends over the through opening 78 is lit up from behind/the interior. The symbol which is attached to the receipt surface 22 is then backlit and signalizes the corresponding information.

FIG. 7, which shows a section through the inventive light curing device in the area of the control element 44, shows that the actuating member 26 and therefore also the cover 30 are considerably narrower at this point. But still, the shape of the cover 30 is also substantially hat-shaped in a cross-section, and the flanges 102 and 104 extend parallel to the housing 12 along its inner wall.

Via the actuating member 26 the control element 44 and the installed switch or button located there are actuated upon pressure on the cover 30. Via conductor paths on the printed circuit 52 which are not shown the related control information is passed on to the not-illustrated control device.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. Light curing device comprising:
    a housing (12),
    at least one control element (44, 46) for controlling the operation of the light curing device (10) and
    an actuating member (26) which is mounted moveably relative to the housing (12) for the actuation of the control element (44, 46),
    wherein at least two control elements (44, 46) are spaced apart from each other and are electrically connected in parallel,
    wherein at least one of the control elements (44, 46) can be actuated by actuation of the actuating member (26), and
    wherein the light curing device contains no more than one actuating member (26) and
wherein at least one of the control elements (44, 46) or both control elements (44, 46) together can be actuated by actuation of the single actuating member (26),
    wherein the control elements (44, 46) are provided with spring-loaded switching elements (48, 50) which can be actuated via the actuating member (26).

2. Light curing device according to claim 1, wherein the light curing device is a hand-held light curing device.

3. Light curing device according to claim 1, wherein the spring-loaded switching elements (48, 50) comprise a rocker or a plunger for actuation.

4. Light curing device according to claim 1, wherein at least one part of the actuating member (26) extends between the control elements (44, 46) and at least one part of the actuating member (26) protrudes beyond the outer contour of the control elements (44, 46).

5. Light curing device according to claim 1, wherein the actuating member (26) extends over the control elements (44, 46) in a beam- or bridge-like manner and is supported by the control elements.

6. Light curing device according to claim 1, wherein the actuating member (26) is mounted moveably in the actuating direction of the control elements (44, 46) relative to a printed circuit (52) which is disposed in the housing (12) whereas the path of movement of the actuating member (26) is limited by stops (90, 92) which are fixed to the housing and/or by the printed circuit (52) and/or by stops of the control elements.

7. Light curing device according to claim 1, comprising guide elements (60, 62) that serve to movably mount the actuating member (26) which prevent a movement of the actuating member (26) in a direction transverse to the actuating direction of the control elements (44, 46), and allow a tilting movement of the actuating member (26).

8. Light curing device according to claim 7, further comprising two pins which protrude from the actuating member (26) and project into corresponding through openings (78, 80, 82 and 84) in the printed circuit (52).

9. Light curing device according to claim 7, wherein the actuating member (26) comprises an non-transparent or opaque material, and wherein on the side of the through openings (78, 80, 82 and 84) which is opposite to the light emitting elements the actuating member (26) is provided with a cover onto which markings (28) or symbols (34*a* to 34*d*) are attached and on which exposure times in the form of numbers are identifiable.

10. Light curing device according to claim 9, wherein the cover (30) in front of the through openings (78, 80, 82, 84) is transparent at the positions where the markings (28) or symbols (34*a* to 34*d*) are attached.

11. Light curing device according to claim 10, wherein the cover (30) is non-transparent or opaque in the areas that are not transparent.

12. Light curing device according to claim 1, wherein at least one light emitting element and the control elements (44, 46) are attached to the printed circuit (52) and supported by it, and that the actuating member (26) is provided with at least one light through opening (78, 80, 82 and 84), whose middle longitudinal axis is in alignment with the light emission axis of the light emitting element.

13. Light curing device according to claim 12, wherein the at least one light emitting element comprises several light emitting elements, and wherein the at least one light through opening comprises several light through openings.

14. Light curing device according to claim 12, wherein the light through openings (78, 80, 82 and 84) for optically decoupling the light emitting elements from one another are provided at a position of height such that one light emitting element each projects into one light through opening (78, 80, 82 and 84).

15. Light curing device according to claim 12, wherein the actuating member (26) maintains a lateral distance relative to the light emitting elements even when actuating only one control element (44, 46) by pressing down one side of the actuating member (26).

16. Light curing device according to claim 1, wherein the cover (30) is supported in a vertical direction at the inner side of the housing (12) and wherein the cover (30) limits the vertical movability of the actuating member (26).

17. Light curing device according to claim 1, wherein upon actuating the actuating member (26) the light emitting elements light up successively and wherein the lighting up of a light emitting element symbolizes a certain operating state and/or an exposure time.

18. Light curing device according to claim 1, wherein upon actuation of the switch (48, 50) or button the operating state of at least one light emitting element is changed as an optical confirmation, and one light emitting element is turned off and an adjacent light emitting element is turned on.

19. Light curing device according to claim 1, wherein the control element (44, 46) is formed by an electric switch (48, 50) or an electric button and/or the light emitting elements are formed by light diodes (LED).

20. Light curing device according to claim 19, wherein the light diodes comprise LED chips (70, 72, 74 and 76).

21. Light curing device according to claim 1, wherein the cover (30) comprises an elastic material.

22. Light curing device according to claim 21, wherein the elastic material comprises silicone.

23. Light curing device comprising:
a housing (12),
at least one control element (44, 46) for controlling operation of the light curing device (10) and
an actuating member (26) which is mounted moveably relative to the housing (12) for the actuation of the control element (44, 46),
guide elements (60, 62) that serve to movably mount the actuating member (26) which prevent a movement of the actuating member (26) in a direction transverse to the actuating direction of the control elements (44, 46), and allow a tilting movement of the actuating member (26),
wherein at least two control elements (44, 46) are spaced apart from each other and are electrically connected in parallel,
wherein at least one of the control elements (44, 46) can be actuated by actuation of the actuating member (26),
wherein the actuating member (26) comprises an non-transparent or opaque material, and
wherein on a side of the through openings (78, 80, 82 and 84) which is opposite to light emitting elements the actuating member (26) is provided with a cover onto which markings (28) or symbols (34*a* to 34*d*) are attached and on which exposure times in the form of numbers are identifiable.

24. Light curing device according to claim 23, wherein a cover (30) in front of the through openings (78, 80, 82, 84) is transparent at the positions where the markings (28) or symbols (34*a* to 34*d*) are attached.

25. Light curing device according to claim 24, wherein the cover (30) is non-transparent or opaque in the areas that are not transparent.

\* \* \* \* \*